US011152103B1

(12) United States Patent
Neumann

(10) Patent No.: US 11,152,103 B1
(45) Date of Patent: Oct. 19, 2021

(54) SYSTEMS AND METHODS FOR GENERATING AN ALIMENTARY PLAN FOR MANAGING MUSCULOSKELETAL SYSTEM DISORDERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,245

(22) Filed: Dec. 29, 2020

(51) Int. Cl.
*G16H 20/60* (2018.01)
*G16H 50/20* (2018.01)
(Continued)

(52) U.S. Cl.
CPC ............ *G16H 20/60* (2018.01); *A61B 5/1118* (2013.01); *A61B 5/486* (2013.01); *A61B 5/4866* (2013.01);
(Continued)

(58) Field of Classification Search
CPC ........ G16H 50/30; G16H 20/60; G16H 10/40; G16H 50/00; G16H 20/00
See application file for complete search history.

(56) References Cited

U.S. PATENT DOCUMENTS

| | | |
|---|---|---|
| 2008/0171319 A1 | 7/2008 | Urdea |
| 2011/0218116 A1 | 9/2011 | Cook |

(Continued)

FOREIGN PATENT DOCUMENTS

WO    WO-2019035125 A1 *  2/2019  ............ G16H 50/30

OTHER PUBLICATIONS

Sampa, Masuda Begum, et al. "Blood Uric Acid Prediction With Machine Learning: Model Development and Performance Comparison." JMIR medical informatics 8.10 (2020): e18331. (Year: 2020).*

(Continued)

*Primary Examiner* — Elaine Gort
*Assistant Examiner* — Constantine B Siozopoulos
(74) *Attorney, Agent, or Firm* — Caldwell Intellectual Property Law, LLC

(57) ABSTRACT

A system for generating a comestible plan to manage musculoskeletal system disorders is disclosed. The system comprises a computing device configured to receive an input comprising physiological data. Computing device may generate a physiological data classifier, Computing device may classify, using the physiological data classifier, the physiological data to a class of physiological data relating to musculoskeletal disorders. Computing device may extract a plurality of biological determinants of a disease state from the physiological data, wherein the plurality of biological determinants includes at least one biological determinant related to at least one disorder located in musculoskeletal system. Computing device may determine a biological determinant concentration. Computing device may identify a musculoskeletal system disorder based on the at least one biological determinant and the biological determinant concentration. Computing device may generate a comestible plan as a function of a positive result for the musculoskeletal system disorder.

18 Claims, 7 Drawing Sheets

(51) Int. Cl.
*G06N 20/00* (2019.01)
*G16H 10/60* (2018.01)
*G16H 70/60* (2018.01)
*G16H 50/50* (2018.01)
*G16H 50/30* (2018.01)
*G01N 33/483* (2006.01)
*A61B 5/11* (2006.01)
*A61B 5/00* (2006.01)
*G16H 10/40* (2018.01)
*G16H 10/20* (2018.01)
*G16H 40/67* (2018.01)

(52) U.S. Cl.
CPC ........... *G01N 33/483* (2013.01); *G06N 20/00* (2019.01); *G16H 10/40* (2018.01); *G16H 10/60* (2018.01); *G16H 50/20* (2018.01); *G16H 50/30* (2018.01); *G16H 50/50* (2018.01); *G16H 70/60* (2018.01); *G16H 10/20* (2018.01); *G16H 40/67* (2018.01)

(56) References Cited

U.S. PATENT DOCUMENTS

| | | | |
|---|---|---|---|
| 2012/0053073 | A1 | 3/2012 | Kassis |
| 2014/0310019 | A1 | 10/2014 | Blander |
| 2016/0012748 | A1 | 1/2016 | Donavon |
| 2016/0259909 | A1* | 9/2016 | Apte ..................... G16H 50/20 |
| 2017/0168070 | A1 | 6/2017 | Oberoi |
| 2019/0304000 | A1 | 10/2019 | Simpson |
| 2020/0400682 | A1* | 12/2020 | Oberoi ................... G16B 40/00 |

OTHER PUBLICATIONS

Reference Notes: https://bmcmusculoskeletdisord.biomedcentral.com/articles/10.1186/s12891-019-2510-7 Title: Strategies for optimising musculoskeletal health in the 21 st century Date: Apr. 11,2019 By: Lewis, Rebecca.

Reference Notes: https://www.ncbi.nlm.nih.gov/pmc/articles/PMC6936212/ Title: Phenotypes of osteoarthritis—current state and future implications Date: Oct. 15, 2019 By: Deveza, Leticia A.

Reference Notes: https://www.sciencedirect.com/science/article/pii/S0261561417302996 Title: Does nutrition play a role in the prevention and management of sarcopenia? Date: Aug. 24, 2017 By: Robinson, Sian M.

Reference Notes: https://academic.oup.com/rheumatology/article/57/suppl_4/iv61/4975692 Title: What is the evidence for a role for diet and nutrition in osteoarthritis? Date: Apr. 17, 2018 By: Thomas, Sally.

Reference Notes: https://link.springer.com/article/10.1186/s13018-017-0567-2 Title: A survey of proteomic biomarkers for heterotopic ossification in blood serum Date: May 4, 2017 By: Edsberg, Laura E.

Reference Notes: https://www.sciencedirect.com/science/article/pii/S1672022918301438 Title: A systems biology approach for studying heterotopic ossification: proteomic analysis of clinical serum and tissue samples Date: Jul. 24, 2018 By: Crowgey, Erin L.

Reference Notes: https://www.ncbi.nlm.nih.gov/pmc/articles/PMC7014986/ Title: The Importance of HLA-B27 in the Evolution of Reactive Arthritis Date: Dec. 30, 2019 By: Bnicioiu-Covei.

Reference Notes: https://www.sciencedirect.com/science/article/pii/S0009898119321503 Title: Serum Deoxyribonuclease 1-like 3 is a potential biomarker for diagnosis of ankylosing spondylitis Date: Nov. 30, 2019 By: Sun.

Reference Notes: https://journals.plos.org/plosone/article?id=10.1371/journal.pone.0229997 Title: Prognostic role of blood KL-6 in rheumatoid arthritis-associated interstitial lung disease Date: Mar. 12, 2020 By: Kim.

Reference Notes: http://www.sarcoidosaserbia.com/wp-content/uploads/2019/03/VERIFYING-SARCOIDOSIS-ACTIVITY-CHITOTRIOSIDASE-VERSUS-ACE.pdf Title: Verifying sarcoidosis activity: Chitotriosidase versus ACE in sarcoidosis—a case-control study Date: Oct. 1, 2016 By: Popevi.

* cited by examiner

SYSTEMS AND METHODS FOR GENERATING AN ALIMENTARY PLAN FOR MANAGING MUSCULOSKELETAL SYSTEM DISORDERS

FIELD OF THE INVENTION

The present invention generally relates to the field of nutrition for disease management. In particular, the present invention is directed to a system and method for generating an alimentary plan to manage a musculoskeletal system disorder.

BACKGROUND

Nutrition is an essential function of life as it provides the necessary nutrients the body needs to sustain all functions of life. The use of artificial intelligence in the field of nutrition may assist in the development and management of a healthy lifestyle for an individual.

SUMMARY OF THE DISCLOSURE

In an aspect of the disclosure, a system for generating a comestible plan to manage musculoskeletal system disorders is disclosed. The system comprises a computing device configured to receive an input comprising physiological data. Computing device may generate a physiological data classifier, where generating the classifier includes receiving physiological data training data correlating physiological data to classes of physiological data that relate to musculoskeletal disorders and training the physiological data classifier using the physiological data training data. Computing device may classify, using the physiological data classifier, the physiological data to a class of physiological data relating to musculoskeletal disorders. Computing device may extract a plurality of biological determinants of a disease state from the physiological data, wherein the plurality of biological determinants includes at least one biological determinant related to a disease state comprising at least one disorder located in musculoskeletal system. Computing device may determine a biological determinant concentration for each biological determinant of the plurality of biological determinants. Computing device may identify a musculoskeletal system disorder based on the at least one biological determinant and the biological determinant concentration. Computing device may generate a comestible plan as a function of a positive result for the musculoskeletal system disorder.

In another aspect of the invention, a method for generating a comestible plan to manage musculoskeletal system disorders is disclosed. The method may generate a physiological data classifier, where generating the classifier includes receiving physiological data training data correlating physiological data to classes of physiological data that relate to musculoskeletal disorders and training the physiological data classifier using the physiological data training data. The method may classify, using the physiological data classifier, the physiological data to a class of physiological data relating to musculoskeletal disorders. The method may extract a plurality of biological determinants of a disease state from the physiological data, wherein the plurality of biological determinants includes at least one biological determinant related to a disease state comprising at least one disorder located in musculoskeletal system. The method may determine a biological determinant concentration for each biological determinant of the plurality of biological determinants. The method may identify a musculoskeletal system disorder based on the at least one biological determinant and the biological determinant concentration. The method may generate a comestible plan as a function of a positive result for the musculoskeletal system disorder.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a comestible to manage musculoskeletal disorders. The system may include a computing device that may receive an input including physiological data which may be in the form of plasma, synovial fluid, MRI data, and the like. A machine-learning classifier may be used to classify any physiological data into physiological data related to musculoskeletal system disorders. The physiological data may contain at least one biological determinant that may be indicative of a musculoskeletal system disorder. A biological determinant concentration may be determined for each biological determinant. The biological determinant concentration may be referenced from the literature or experimentally obtained. Based on a biological determinant and the biological determinant concentration a musculoskeletal system disorder is determined, and a comestible plan is generated.

A practical application of this technology includes the use of a machine-learning model to provide a user access to comestible plans that may improve and/or and/or relieve symptoms related to a musculoskeletal system disorder. The systems and methods allow for an update of the comestible plan if the musculoskeletal system disorder does not improve.

Figure 1:
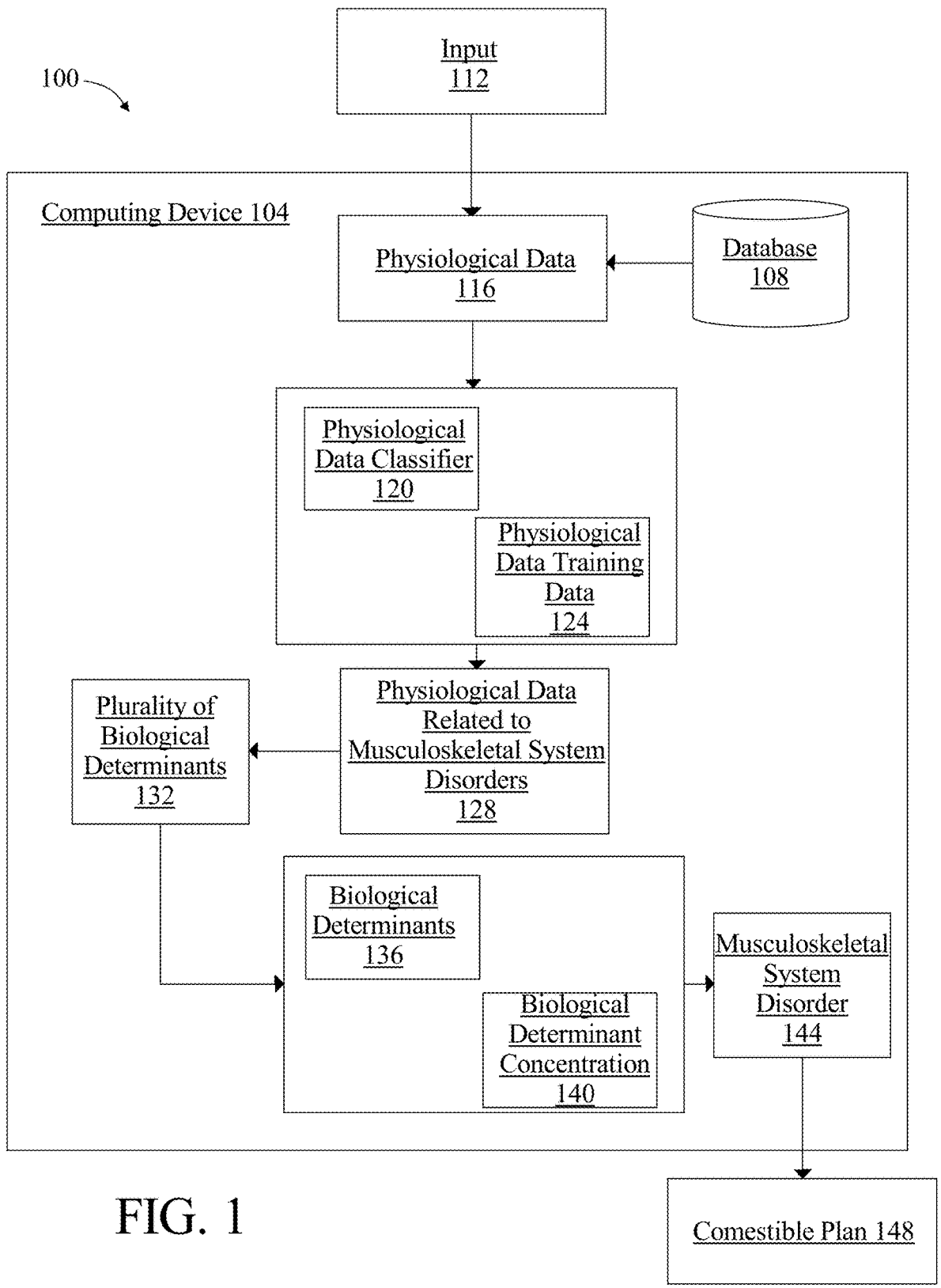
FIG. 1 is a block diagram of an exemplary embodiment of a system of determining a comestible plan to manage a musculoskeletal system disorder.

Referring now to FIG. 1, an exemplary embodiment of a system 100 for generating an alimentary plan for managing a musculoskeletal system disorder is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting a computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
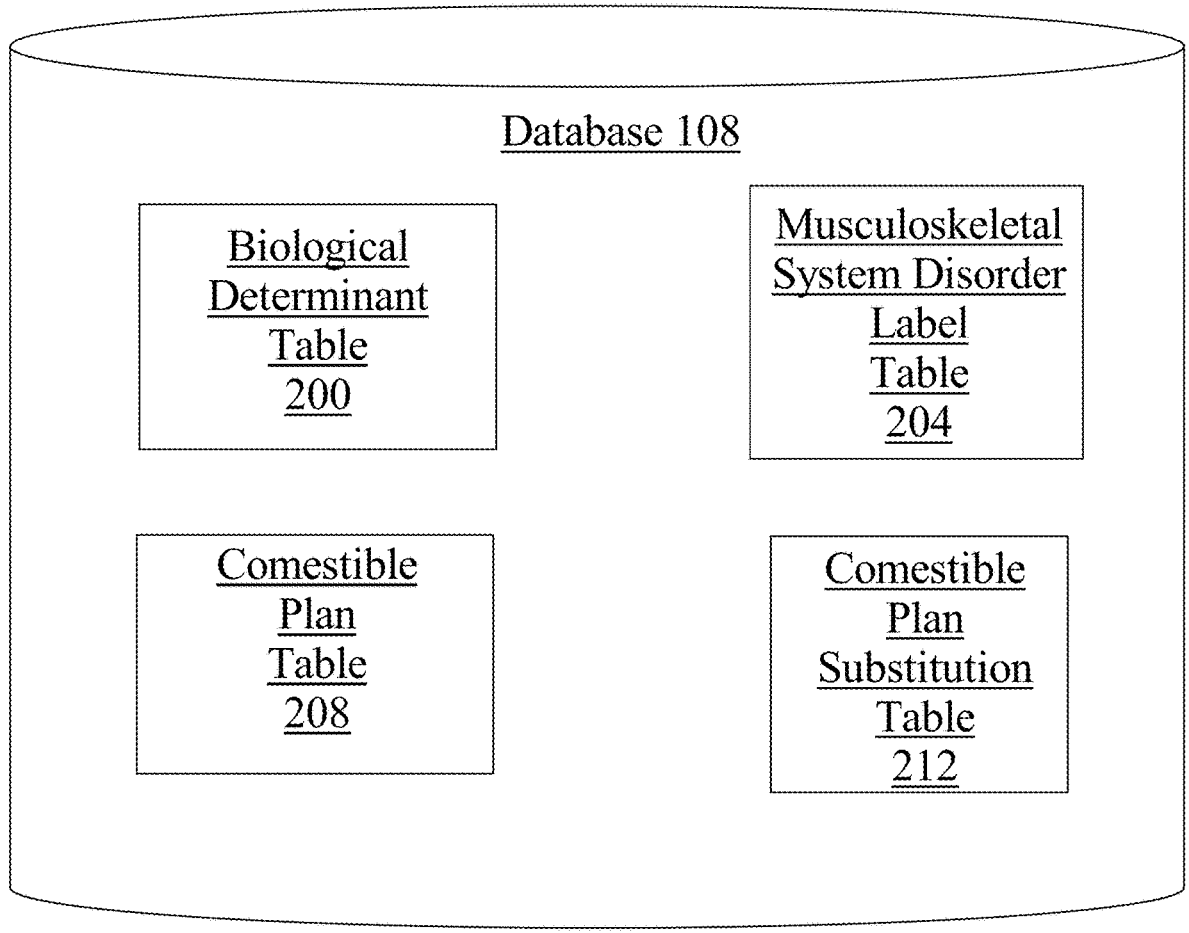
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, a biological determinant table 200. Biological determinant table 200 may be used to store biological determinants and corresponding analytical assay, or the like. As another non-limiting example, one or more tables in database 108 may include a musculoskeletal system disorder label table 204. Musculoskeletal system disorder label table 204 may be used to store correlations between biological determinants and potential musculoskeletal system disorder, and the like. Another non-limiting example, one or more tables in database 108 may include an comestible plan table 208. Comestible plan table 208 may include, but not limited to comestible combinations that may treat or prevent a specific musculoskeletal system disorder, adverse foods affecting musculoskeletal system disorder, and the like. As another non-limiting example, one or more tables in database 108 may include comestible plan substitution table 212. Comestible plan substitution table 212 may include comestible combinations that may include allowable substitutions for comestible combinations, substitutions that may create an adverse effect on a musculoskeletal system disorder, and the like.

With continued reference to FIG. 1, computing device 104 may be configured to receive an input 112. An "input," as used in this disclosure, may include, but not limited to any medical test, a user's health assessment, a user's nutritional assessment, an assessment conducted in any website related to a musculoskeletal system disorder condition, a direct entry from a user, and the like. Input 112 may include physiological data 116. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in each medical field as useful for identifying various disease conditions or prognoses within a relevant field. As a non-limiting example, and without limitation, physiological data 116 describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chatrooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genetics test data. As used in this disclosure, genetics test data involves data related to genetics which may show a pre-disposition for any type of disease such as, for example, but not limited to, a musculoskeletal system disorder. Genetics data may include, but not limited to, deoxyribonucleic acid (DNA) samples and/or sequences, such as without limitation DNA sequences contained in one or more chromosomes in human cells. Genetics test data may include, without limitation, ribonucleic acid (RNA) samples and/or sequences, such as samples and/or sequences of messenger RNA (mRNA) or the like taken from human cells. Genetics test data may include telomere lengths. Genetics test data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data 116 may include, without limitation any result of any medical test, physiological assessment, cognitive assessment, psychological assessment, nutritional assessments, mobility assessments, or the like. For instance, and without limitations, a mobility assessment may include a posture assessment to observe a deficiency in the curvature of the spine, or to study muscle strength. A mobility assessment may also include a study of the user's range of motion of, for example, an upper or lower limb. A color, warmth, movement, and sensation ("CWMS") assessment may suggest an articular injury or disease. A mobility assessment may include the inspection of the arms and legs for pain, deformity, edema, pressure areas, and bruises. Another type of mobility assessment may include assessment of motor power through hand grip, dorsi and plantar flexion, and knee and hip flexion against resistance. Another mobility assessment may be measuring leg strength. General leg strength may be assessed by asking a user to dosiflex while a medical practitioner applies resistance to the bottom of the feet. In another example, data from a nutritional assessment may be used to identify foods, beverage, supplements, and the like, and generate a musculoskeletal index. As used in this specification, a "musculoskeletal index" is a measure on the impact of foods, beverages, supplements, and the like on symptoms of a musculoskeletal system disorder and/or to establish the progression of a disease. For example, red meats may impact the musculoskeletal index negatively, as a diet that includes red meats may exacerbate joint problems such as gout.

Additionally and with reference to FIG. 1. input 112 may include at least a physiological data 116 from one or more other devices after performance; system 100 may alternatively or additionally perform one or more assessments and/or tests to obtain at least a physiological data 116, and/or one or more portions thereof, on system 100. For instance, at least physiological data 116 may include or more entries by a user in a form or similar graphical user interface object; one or more entries may include, without limitation, user responses to questions on a psychological, behavioral, personality, or cognitive test. For instance, at least a computing device 104 may present to user a set of assessment questions designed or intended to evaluate a current state of mind of the user, a current psychological state of the user, a personality trait of the user, or the like; at least a computing device 104 may provide user-entered responses to such questions directly as at least a physiological data 116 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data 116 may include data describing one or more test results, such as for example, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data 116 may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge, and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's *muciniphila, Anaerotruncus colihominis*, bacteriology, *Bacteroides* vulgates', *Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, computing device 104 may generate a physiological data classifier 120. Computing device 104 may receive physiological data training data 124 correlating physiological data to classes of physiological data that relate to musculoskeletal system disorders. As used in this disclosure, "classes of physiological data that relate to musculoskeletal system disorders" refers to physiological data that contains biological determinants that may aid in determining a type of musculoskeletal system disorder. Classes of physiological data that relate to musculoskeletal system disorders may include, but not limited to, hematological data which may include a blood sample, a plasma sample, and the like. Other examples include radiology data, such as an X-ray, an MM, a CT scan, and the like. Physiological data training data 124 may be received and/or collected from experts or from users that may have received and used an alimentary plan. Physiological data training data 124 may be received as a function of user-entered valuations of alimentary plans, alimentary plan metrics, and/or measurable values. Physiological data training data 124 set may be received by one or more past iterations of the previous physiological data training data vectors. Physiological data training data 124 may be received by one or more remote devices that at least correlate physiological data element and classes of physiological data to a measurable value, wherein a remote device is an external device to computing device 104. "Training data," as used herein, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 132 according to various correlations; correlations may indicate causative and/or predictive links between categories of data elements, which may be modeled as relationships such as mathematical relationships by machine learning processes as described in further detail below. Training data 132 may be formatted and/or organized by categories of data elements, for instance by associating data elements with one or more descriptors corresponding to categories of data elements. As a non-limiting example, training data 132 may include data entered in standardized forms by persons or processes, such that entry of a given data element in a given field in a form may be mapped to one or more descriptors of categories. Elements in training data 132 may be linked to descriptors of categories by tags, tokens, or other data elements; for instance, and without limitation, training data 132 may be provided in fixed-length formats, formats linking positions of data to categories such as comma-separated value (CSV) formats and/or self-describing formats such as extensible markup language (XML), enabling processes or devices to detect categories of data.

Alternatively or additionally, and with continued reference to FIG. 1, training data 132 may include one or more elements that are not categorized; that is, training data 132 may not be formatted or contain descriptors for some elements of data. Machine learning algorithms and/or other processes may sort training data 132 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 132 to be made applicable for two or more distinct machine learning algorithms as described in further detail below. Training data 132 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs. Computing device 104 may train physiological data classifier 120 using physiological data training data 124. A description on machine learning and the use of classifiers follows below.

Figure 3:
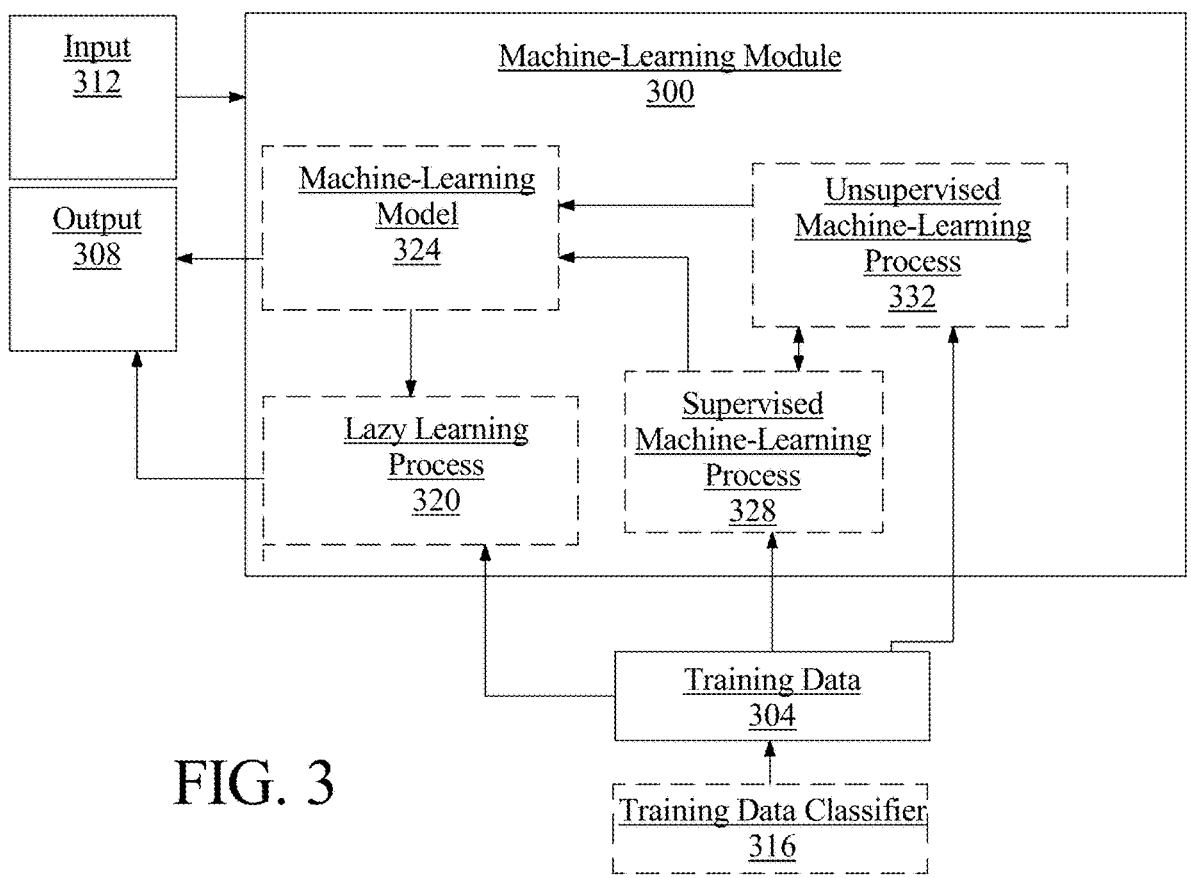
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, musculoskeletal biological determinants may serve as inputs, outputting other potential health disorders that a may use the same biological determinants.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify a musculoskeletal system disorder into categories such as a bone disorder, a joint disorder; a musculoskeletal system disorder related to another disease state, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a biological determinants such as citrullinated protein (CP) as described above as inputs, with at least rheumatoid arthritis as outputs of a musculoskeletal system disorder, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring back to FIG. 1, computing device 104 may classify, using physiological data classifier 120, the physiological data to a class of physiological data related to musculoskeletal system disorders 128. The use of classifiers may be implemented, without limitation, as described earlier in this disclosure. For instance, inputs such as, but not limited to, plasma, blood, synovial fluid, X-rays, an MM, a mobility assessment, a CT scan, a bone scan, an ultrasound, arthroscopy, results of a joint aspiration study, results of nerve conduction studies, muscle tests. or the like may be a class of physiological data related to a musculoskeletal system disorder 128. Conversely, a stool sample or a urine sample may not be a class of physiological data related to a musculoskeletal system disorder 128. Physiological data related to a musculoskeletal system disorder 128 may be classified further, for example, into physiological data related to another condition or disease, physiological data indicating a specific musculoskeletal system disease, and the like. For example, a plasma sample may contain an abnormal concentration of citrullinated protein ("CP") which may indicate that the user may have rheumatoid arthritis; the plasma sample may also contain abnormal levels of amyloid beta-protein (A beta), A beta autoantibodies, platelet amyloid precursor protein (APP) isoforms which may indicate a user potentially suffering from Alzheimer's disease.

Alternatively or additionally, computing device 104 may be configured to generate a musculoskeletal system disorder classifier by receiving musculoskeletal system disorder training data correlating a musculoskeletal system disorder and biological determinant concentration to musculoskeletal system disorder labels. The use of classifiers may be implemented, without limitation, as described earlier in this disclosure. Musculoskeletal system disorder training data may be received and/or collected from experts or from users that may have received and used in a comestible plan. Musculoskeletal system disorder training data may be received as a function of user-entered valuations of comestible plans, comestible plan metrics, and/or measurable values. Musculoskeletal system disorder training data set may be received by one or more past iterations of the previous musculoskeletal system disorder training data training data vectors. Musculoskeletal system disorder training data may be received by one or more remote devices that at least correlate musculoskeletal system disorder training data element and classes of musculoskeletal system disorder training data to a measurable value, wherein a remote device is an external device to computing device 104. As used in this disclosure, "musculoskeletal system disorder labels" are elements of data that may be used to tag a musculoskeletal system disorder. For example, elevated levels of inflammatory cytokines and C-reactive protein may be tagged with the label "Musculoskeletal system inflammation." Computing device 104 may classify, using the musculoskeletal system disorder classifier, the at least one biological determinant and the biological determinant concentration to a positive result for a musculoskeletal system disorder. A "positive result," as defined by this disclosure, is a test result where at least one biological determinant for a musculoskeletal system disorder may be found. A positive result may indicate that the user may be presently suffering from a musculoskeletal system disorder. Alternatively, a positive result may also indicate that the user may develop a musculoskeletal system disorder in the future. For example, a positive test for osteoarthritis may indicate increased levels of biological determinants such as CRP, pyridinoline, YKL-40, MMP-3 and TIMP-1. The use of classifiers and machine-learning models has been described earlier in this disclosure.

Still with reference to FIG. 1, computing device 104 may be configured to extract a plurality of biological determinants 132 of a disease state from the physiological data related to musculoskeletal system disorders 128. Plurality of biological determinants 132 includes at least one biological determinant 136 related to a disease state comprising at least one disorder located in musculoskeletal system. As used in this disclosure, a "musculoskeletal system disorder" is any anomaly or any injury or disorder of a group which may include, but not limited to, muscles, nerves, tendons, joints, cartilage, spinal disks, and the like. Examples of musculoskeletal system disorders include, but are not limited to tendinitis, carpal tunnel syndrome, osteoarthritis, rheumatoid arthritis, fibromyalgia, bone fractures, muscle and tendon sprains, ligament sprains, tension neck syndrome, thoracic outlet compression, radial tunnel syndrome, trigger finger, degenerative disc disease, herniated disks, and the like. Musculoskeletal system disorders may be a secondary condition associated with another disease state. For example, plaque psoriasis, is an auto-immune disorder which causes skin cells to multiply up to 10 times faster than normal. This makes the skin build up into bumpy red patches covered with white scales. Psoriatic arthritis, also an auto-immune condition, may develop as an inflammation causing stiffness in the joints, and its onset is associated with psoriasis. Persons skilled in the art, upon reviewing the entirety of this disclosure, will be aware of additional causes of other musculoskeletal disorders. A "biological determinant," as used in this disclosure, is a biological element found in any body fluid, for example blood, synovial fluid, spinal fluid, or the like, that indicates the presence or absence of a condition or a disease. Biological determinants 136 may include, for example, monitoring biological determinants. A "monitoring biological determinant," as used in this specification, is a biological determinant that may be used to assess the progress of a disease or to monitor the effects of a therapeutic agent, such as, for example, a platelet-rich plasma treatment. In another example, a biological determinant 136 may be a diagnostic biological determinant. A "diagnostic biological determinant," as defined in this disclosure is a biological determinant that is used to detect the presence of a disease or a condition of interest. In an embodiment, the plurality of biological determinants 132 comprises a diagnostic determinant. Another example of a biological determinant 136 is a predictive biological determinant. A "predictive biological determinant," as used in this disclosure, is a biological determinant used to predict what group of patients will respond favorably or unfavorably to a particular treatment. Examples of biological determinants that may be used in diagnosing a musculoskeletal system disorder may include, but are not limited as C reactive protein, HLA-B27, DNASE1L3, dihydropyridine dehydrogenase, protein c, osteocalcin, alpha-2 type I collagen, collagen alpha-1(V) chain isoform 2 pre-protein, bone sialoprotein 2, phosphatide phosphatase LPIN2, osteomodulin, protein phosphatase 1J, RRP12-like protein, sACE, KL-6, Chitotriosidase, ACE, lysozyme, and the like.

Additionally or alternatively, and with continued reference to FIG. 1, lifestyle behaviors of a user may result in a musculoskeletal system disorder. For instance, a user may consume a diet heavy in red meats, organ meats, and seafood. This may cause the concentration of uric acid to rise which may lead to a condition known as gout which affects the joints. As another example, cigarette smoking may lead to decreased levels of estrogen and testosterone and the parathyroid hormone which may lead to a loss of bone mineral content. In an embodiment, lifestyle training data correlating activities to musculoskeletal system disorders may be used to train a machine-learning model. A user activity may serve as an input outputting a potential musculoskeletal system disorder based on the trained machine-learning model. In addition, a lifestyle classifier may be trained using, for example, cohort data correlating musculoskeletal system disorder to users experiencing the musculoskeletal system disorder to lifestyle activities. Using the lifestyle classifier, musculoskeletal system disorders may be classified to a corresponding lifestyle activity. The use of machine-learning models and classifiers was discussed earlier in this disclosure.

With continued reference to FIG. 1, computing device 104 may determine biological determinant concentration 140 for each biological determinant 136 of the plurality of biological determinants 132. As used in this disclosure, a "biological determinant concentration" is defined as the concentration of a biological determinant in any physiological data that may be used a measure of the presence or absence of a musculoskeletal system disorder. For instance, a decrease of 7.8% in bone formation biological determinant such as osteocalcin and bone resorption biological determinant such as cross-linked N-telopeptides of bone type I collagen (NTXs) biological determinants may indicate the presence of a musculoskeletal disorder such as osteoporosis. An example of a technique used to determine biological determinant concentration 140 includes electrochemiluminescence ("ECL") where electrochemically generated intermediates undergo an exergonic reaction to produce an electronically excited state that emits light upon relaxation to a lower energy state. The wavelength of the emitted light is measured as it corresponds to the energy gap between the two energy states which results in a measure of the concentration of the emitting biomarker. An example of the use of ECL includes the determination of biological determinant troponin I (sTNI) as a marker for skeletal injuries by using an ECL assay for troponin I and the biological determinant concentration for troponin. Another technique includes analysis by liquid chromatography-mass spectrometry ("LC-MS"). With LC-MS, solubilized compounds (the mobile phase) are passed through a column packed with a stationary (solid) phase. This effectively separates the compounds based on parameters such as the weight of the biological determinant or the affinity of the biological determinant for the mobile phase and the stationary phase. For example, an LC-MS assay may determine the presence of the biological determinant γ-aminobutyric acid (GABA) and (R)-3-aminoisobutyric acid (D-BAIBA) along with the biological determinant concentration. A decreased level of, for example, GABA may be indicative of an osteoporotic fracture. A person skilled in the art would recognize other techniques suitable to determine the concentration of any biological determinant upon review of the entirety of this disclosure.

With continued reference to FIG. 1, computing device 104 may identify musculoskeletal system disorder 144 as a function of the at least one biological determinant and biological determinant concentration. For instance, an enzyme-linked immunosorbent assay ("ELISA") may be used to identify at least one bone-related biological determinant and the biological determinant concentration to determine loss of bone resorption which may indicate a bone-related musculoskeletal disorder. In this example, an increase in the concentration of cross-linked N-telopeptides of bone type I collagen ("NTX") may indicate a bone disorder. Biological determinant concentration 140 indicating a potential musculoskeletal system disorder may be a value published in, for example, a research journal. Alternatively, a biological indicator may be determined by experimentation. For example, a biological determinant concentration for a biological determinant that may indicate a musculoskeletal disorder may incorporate testing for a biological determinant and biological determinant concentration using a control group where there is no known musculoskeletal disorder. Values for the biological determinant concentration for a sample group known to have a musculoskeletal disorder may be compared against the values obtained for the control group and a determination made regarding the presence of a musculoskeletal disorder.

With continued reference to FIG. 1, computing device 104 may generate comestibles plan 148 as a function of a positive result for musculoskeletal system disorder 144. As defined in this disclosure, an "comestible plan" is a set of instructions for consumption of a plurality of comestible compositions that, as used in this disclosure, may help relieve and/or prevent, for example, a musculoskeletal system disorder. "Comestible compositions," as used in this disclosure, may include any combination of ingredients that may be ingested by a user or treated as a meal or a snack or any beverages or combination of beverages that may be consumed by a user. Comestibles plan 148 may include, for example, what type of comestible compositions a user may want to consume based on the desire to relieve and/or prevent a musculoskeletal system disorder. Comestibles plan 148 may include what specific time of the day the user should consume the comestible compositions. Comestible plan 148 may include a list of comestible compositions to avoid based on a positive result for a musculoskeletal disorder. Comestibles plan 148 may include a list of acceptable comestible compositions substitutes in case a comestible composition suggested to the user is not available. Comestible plan may include a list of nutritional supplements that may relieve and/or prevent one or more musculoskeletal system disorder. Comestible plan 148 may include additives to impart flavor. These additives may include, but not limited to, spices such as turmeric, liquid condiments such as soy sauce, fish sauce, and the like. Additives may include sweeteners and/or sweetener substitutes. Sweeteners and sweetener substitutes may include, but not limited to, cane sugar, aspartame, saccharin, rice syrup, agave syrup, and the like. Comestible plan 148 may include information as to how to safely take the supplements as well as information regarding any potential adverse effects. In an embodiment, computing device 104 may receive physical activity data and update the comestible plan as a function of the physical activity data. As used in this disclosure, "physical activity" is defined as body movement produced by skeletal muscle that requires energy. Examples of physical activity include, but are not limited to, exercise, heavy lifting of any object, a measure of the amount of walking steps taken by a user, and the like. For instance, a user may burn more calories as a result of some form of exercise at an established frequency, such as daily, 3 times a week, twice a week, and the like. Computing device 104 may calculate the number of calories burned related to the physical activity data and update the comestible plan based on the physical activity data. Conversely, computing device 104 may adjust the comestible plan as a result of a sedentary lifestyle which may include the performance of no physical activity by the user.

Alternatively or additionally, with reference to FIG. 1, generating comestibles plan 148 may include generating a plurality of comestible compositions as a function of the positive result. Computing device 104 may order the plurality of comestible compositions as a function of a change in biological determinant concentration 140 to a suitable range; ordering may be in ascending or descending order. As used in this disclosure, a "suitable range" is defined as a range of biological determinant concentration 140 that would indicate the absence of musculoskeletal system disorder 144 or that the risk of development of a musculoskeletal system disorder is low. For instance, a comestible plan may include comestible compositions that may help decrease the biological determinant concentration of a biological determinant further which may indicate that the comestible compositions are effective at treating and/or alleviating the symptoms of a musculoskeletal system disorder. Different comestible compositions may not decrease the biological determinant concentration as much. In an embodiment, a score is generated based on the amount of change of the biological determinant concentration, where the amount of change, as used in this specification, is an increase or decrease of the biological determinant concentration into a suitable range that shows an improvement of a musculoskeletal system disorder. In another embodiment, computing device 104 orders the scores based where the comestible compositions that affect the highest change in biological determinant concentration receive the highest score. For example, a user with sarcopenia may have biological determinants IL-6, SPARC, MIF, and IGF-1 present with levels outside a suitable range. A comestible plan that includes comestible compositions rich in protein may relieve and/or prevent sarcopenia by reducing levels of IL-6, SPARC, MIF, and IGF to biological concentration levels in a suitable range. A comestible plan that is high in fats may not be as effective in reducing the biological determinant levels to a suitable range. The plurality of comestible compositions with the highest change to the suitable range receives the highest order. Computing device 104 may assign the comestible plan to the plurality of comestible compositions with the highest order. The alimentary plan assigned by computing device 104 may help relieve and/or prevent a plurality of disorders, which may include, but not limited to other musculoskeletal system disorders, eating disorders, neurological disorders, gastrointestinal disorders, skin conditions, and the like. As an example, a diet rich in protein may help prevent and/or relieve sarcopenia, but, in addition, such a diet may help relieve and/or prevent weight gain which may be associated with a genetic disorder. In one embodiment, the plurality of alimentary compositions may address a plurality of disorders.

Figure 4:
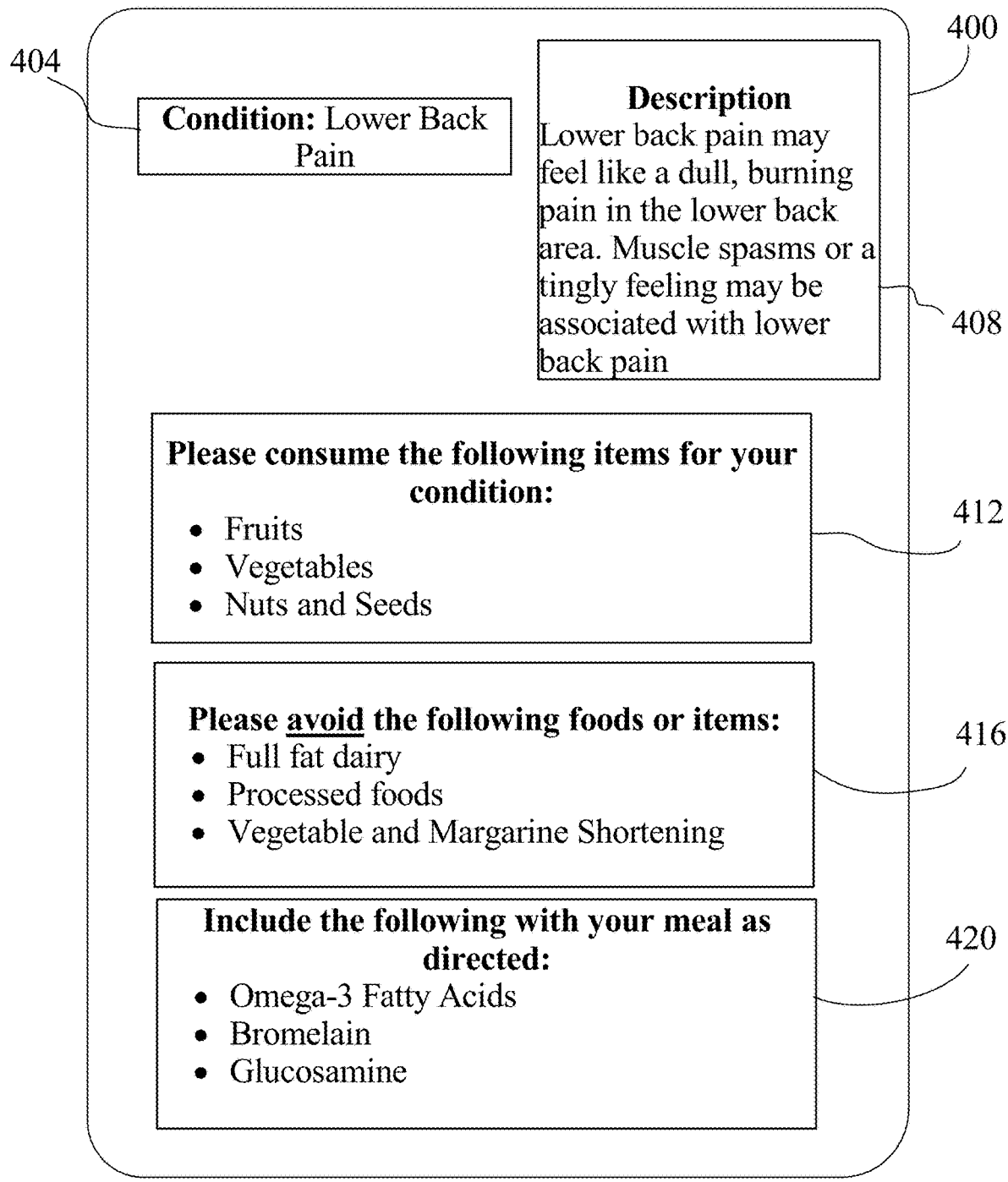
FIG. 4. is a representative illustration of a comestible plan in a GUI-based device.

Referring now to FIG. 4, an exemplary embodiment of comestible plan 148 is described. Comestible plan 148 may be displayed in a user device 400. For instance, comestible plan 148 may be displayed in any GUI-based device, such as, but not limited to a mobile telephone, a tablet computer, a desktop computer, and the like. A user may feel pain due to inflammation and/or been diagnosed with a musculoskeletal system disorder 404 such as, for example, lower back pain. Comestible plan 148 may include description section 408. Description section 408 may describe musculoskeletal system disorder 404. Comestible plan 148 may include comestible compositions 412 for the user to consume to relieve and/or prevent back pain. Comestible plan 148 may include adverse foods 416. Adverse foods 416 may include foods that a user should avoid as the foods listed may aggravate the musculoskeletal system disorder. Nutrients 420 may include a list if supplements that may relieve and/or prevent the musculoskeletal system disorder. Nutrients 420 may include, but not limited to, vitamins, amino acids, minerals, and the like.

Figure 5:
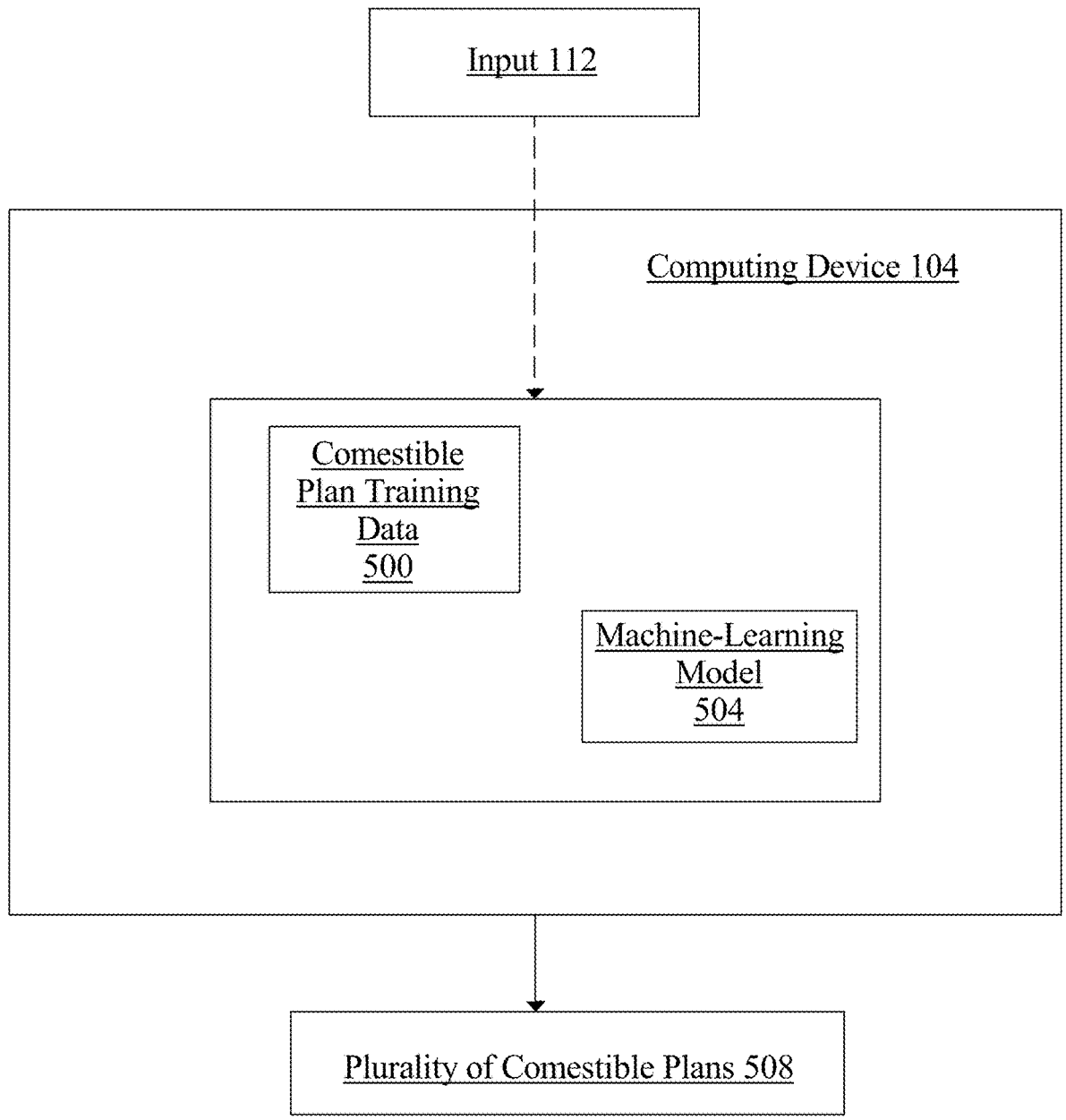
FIG. 5 is a block diagram of an exemplary embodiment of a determination of a plurality of comestible plans as a function of a machine-learning process.

Now referring to FIG. 5, an exemplary embodiment of the generation of a plurality of comestible plans 508 implementing a machine-learning process that may treat and/or prevent and/or relieve a musculoskeletal system disorder is described. Computing device 104 is configured to receive input 112. Computing device 104 may receive comestible plan training data 500. Comestible plan training data 500 may be received and/or collected from experts or from users that may have received and used an comestible plan. Comestible plan training data 500 may be received as a function of user-entered valuations of comestible plans, comestible plan metrics, and/or measurable values. The comestible plan training set may be received by one or more past iterations of the previous comestible plan vectors. The comestible plan training set may be received by one or more remote devices that at least correlate a comestible plan element and musculoskeletal system disorder metric to a measurable value, wherein a remote device is an external device to computing device 104. A machine-learning model 504 is trained using comestible plan training data 500. Comestible plan training data 500 correlates comestible compositions to effects on musculoskeletal system disorders. Plurality of comestible plans 508 is outputted as a function of the machine-learning model. The machine-learning model may be implemented and/or trained, without any limitations, as described earlier in this disclosure. In another embodiment, generating comestible plan 148 may include outputting a message independent of the presence of the plurality of comestible plans. For example, comestible plan training data 500 may not contain values for a particular musculoskeletal system disorder. As a result, plurality of comestible plans 508 would not produce suitable plans to treat and/or prevent the musculoskeletal system disorder. As such, a message may be outputted indicating this condition. The message may be outputted directly to a user device, a web page, an email message, and the like. An example of a message may include, "No nutrition suggestions are available for the entered condition."

Referring back to FIG. 1, computing device 104 may be configured to receive a second input. The second input may include any of the inputs as described for input 112. For example, a second input may correspond to a second synovial fluid sample taken after commencing use of comestible plan 148. A medical professional may want to retest a user to check for changes in the presence or absence of at least one biological determinant for musculoskeletal system disorder 144. A medical professional may want to retest a user to check for changes in biological determinant concentration 140. Computing device 104 may redetermine the at least one biological determinant and biological determinant concentration or musculoskeletal system disorder 144 from the second input. The determination of the at least one biological determinant and biological determinant concentration for a musculoskeletal system disorder was discussed earlier in this disclosure. Computing device 104 may update comestible plan 148 as a function of the second input. The update, may be performed by repeating and/or performing any process step or combination of process steps for generating a comestible plan as described in this disclosure. As a non-limiting example, biological determinant concentration 140 of biological determinant 136 may remain unchanged after implementing comestible plan 148. Comestible plan 148 generated to treat carpal tunnel syndrome which may include, but not limited to fish and other foods high on omega-3 fatty acids, may offer no change in biological determinant concentration 140 for glutathione-insulin transhydrogenase (216AA). Comestible plan 148 may be updated to, for example, add a supplement such as vitamin B6 to comestible plan 148.

Figure 6:
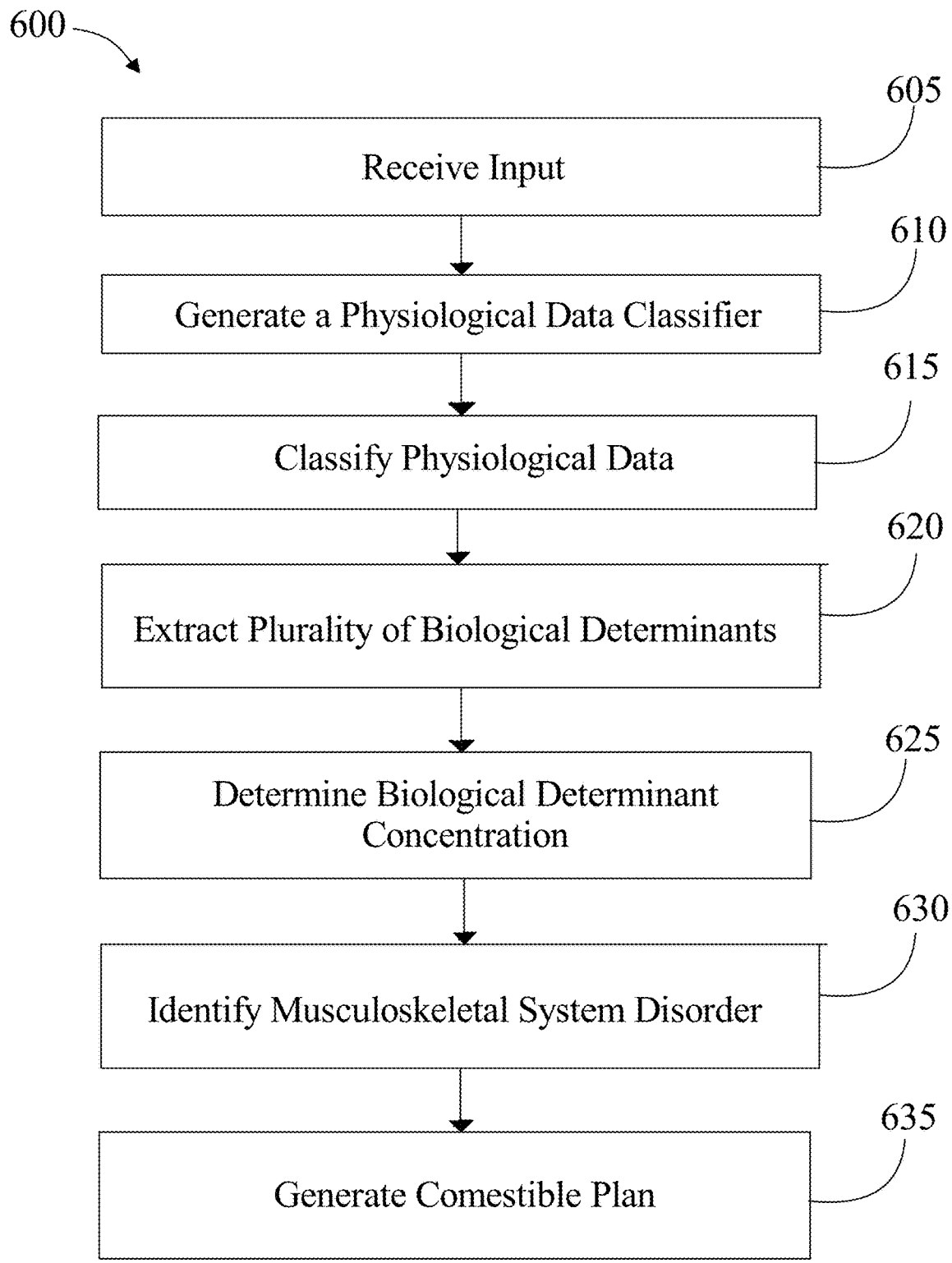
FIG. 6 is a flow diagram illustrating an exemplary embodiment of a method of determining a comestible plan to manage a musculoskeletal system disorder.

Referring now to FIG. 6, an exemplary method 600 for generating a comestible plan to manage musculoskeletal system disorders is described. At step 605, computing device may receive an input. The input may include physiological data. This may be implemented, without limitations, as described in FIGS. 1-5. The physiological data may include genetics test data. The physiological data may include physiological data related to a mobility assessment.

Still referring to FIG. 6, at step 610, computing device may generate a physiological data classifier. The computing device may receive physiological data training data correlating physiological data to classes of physiological data that relate to musculoskeletal system disorders. Computing device may train physiological data classifier using physiological data training data. This step may be implemented, without limitations, as describe in FIGS. 1-5.

With continued reference to FIG. 6, at step 615, computing device may classify, using the physiological data classifier, the physiological data to a class of physiological data related to musculoskeletal system disorders. This step may be implemented, without limitations, as described in FIGS. 1-5. Alternatively or additionally, computing device may be configured to generate a musculoskeletal system disorder classifier by receiving musculoskeletal system disorder training data which correlates a musculoskeletal system disorder and biological determinant concentration to musculoskeletal system disorder labels. Computing device may train the musculoskeletal system disorder classifier using the musculoskeletal disorder training data. Computing device may classify, using the musculoskeletal system disorder classifier, the at least one biological determinant and the biological determinant concentration to a positive result for a musculoskeletal system disorder. The above may be implemented, without limitations, as described in FIGS. 1-5. Computing device may output a message independent of a presence of the plurality of comestibles plans.

Still with reference to FIG. 6, at step 620, computing device may be configured to extract a plurality of biological determinants of a disease state from the physiological data related to musculoskeletal system disorders. The plurality of biological determinants includes at least one biological determinant related to a disease state comprising at least one disorder located in musculoskeletal system. This step may be implemented, without limitation, as described in FIG. 1-5. Alternatively or additionally, lifestyle behaviors of a user may result in a musculoskeletal system disorder. In an embodiment, lifestyle training data correlating activities to musculoskeletal system disorders may be used to train a machine-learning model. A user activity may serve as an input outputting a potential musculoskeletal system disorder based on the trained machine-learning model. In addition, a lifestyle classifier may be trained using, for example, cohort data correlating musculoskeletal system disorder to users experiencing the musculoskeletal system disorder to lifestyle activities. Using the lifestyle classifier, musculoskeletal system disorders may be classified to a corresponding lifestyle activity. The use of machine-learning models and classifiers was discussed earlier in this disclosure.

Referencing still FIG. 6, at step 625, computing device may determine a biological determinant concentration for each biological determinant of the plurality of biological determinants. This step may be implemented, without limitations, as described in FIGS. 1-5.

With continued reference to FIG. 6, at step 630, computing device may identify a musculoskeletal system disorder as a function of the at least one biological determinant and biological determinant concentration. This step may be implemented, without limitations, as described in FIGS. 1-5.

Still referencing FIG. 6, at step 635, computing device may generate a comestibles plan as a function of a positive result. This step may be implemented, without limitations, as described in FIGS. 1-5. Generating a comestibles plan may include generating a plurality of alimentary compositions as a function of the positive result. Computing device may order the plurality of comestible compositions in descending order as a function of a change in the biological determinant concentration to a suitable range. Computing device may assign the comestible plan to the plurality of comestible compositions with the highest order. Computing device may receive physical activity data, and update the comestible plan based on the physical activity data.

Alternatively or additionally, and with continued reference to FIG. 6, computing device may be configured to receive a second input. Computing device may redetermine the at least one biological determinant and biological determinant concentration for musculoskeletal system disorder from the second input. Computing device may update the comestible plan as a function of the second input. The above may be implemented, without limitations, as described in FIGS. 1-5

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
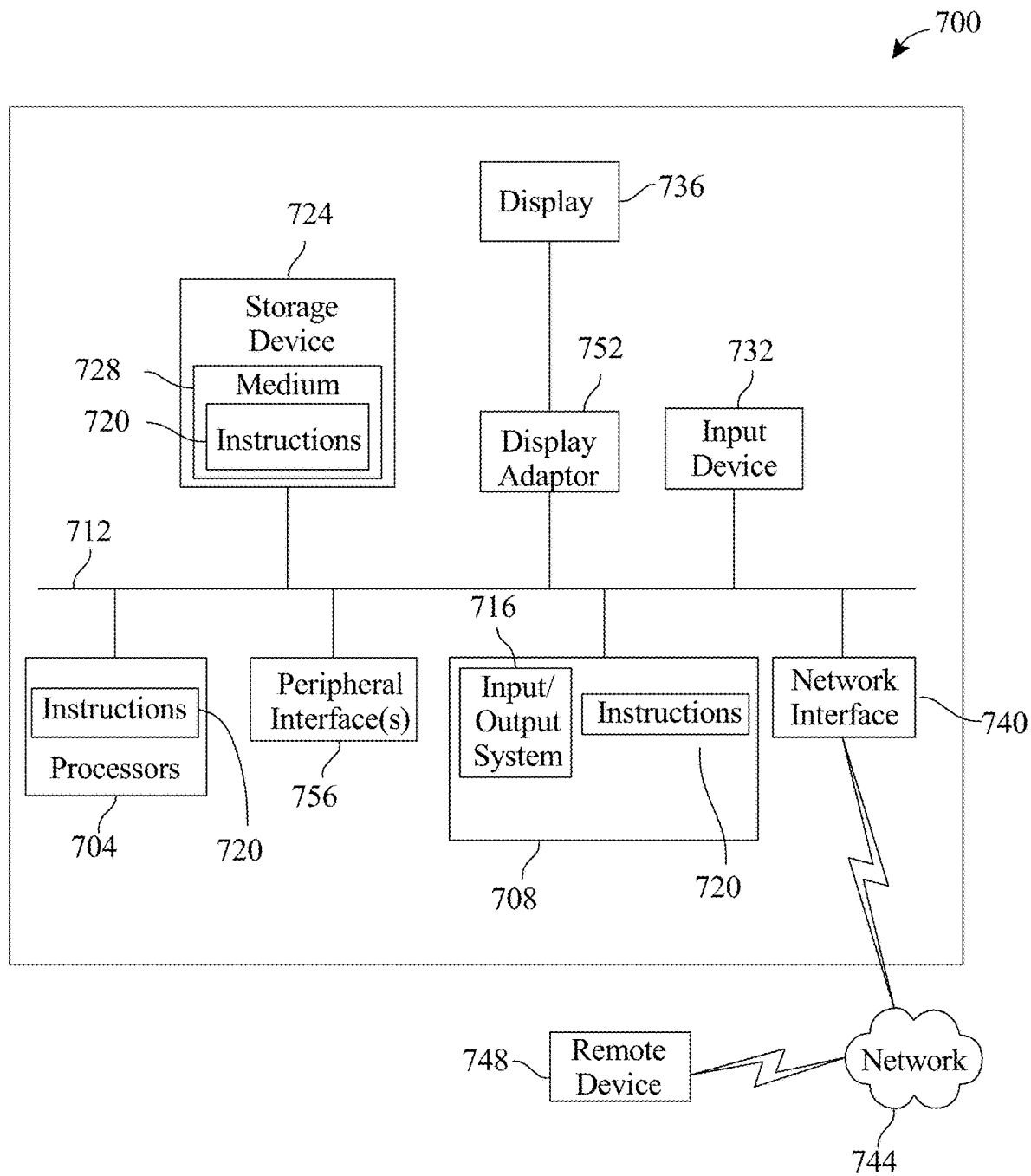
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems, and according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a comestible plan to manage a musculoskeletal system disorder, the system comprising:
 a computing device configured to:
 receive an input comprising physiological data;
 generate a physiological data classifier, where generating the physiological data classifier comprises:
  receiving physiological data training data correlating physiological data to classes of physiological data that relate to musculoskeletal disorders; and
  training the physiological data classifier using the physiological data training data;
 classify, using the physiological data classifier, the physiological data to a class of physiological data relating to musculoskeletal system disorders;
 extract a plurality of biological determinants of a disease state from the class of physiological data relating to musculoskeletal system disorders, wherein the plurality of biological determinants includes at least one biological determinant related to a disease state comprising at least one disorder located in musculoskeletal system;
 determine a biological determinant concentration for each biological determinant of the plurality of biological determinants;
 identify a positive result for a musculoskeletal system disorder as a function of the at least one biological determinant and the biological determinant concentration; and
 generate a comestible plan as a function of the positive result, wherein generating the comestible plan comprises:
  receiving comestible plan training data;
  training a machine-learning model using the comestible plan training data, wherein the comestible plan training data correlates comestible compositions to effects on musculoskeletal system disorders;
  outputting a plurality of comestible compositions as a function of the machine-learning model and the positive result; and
  generating the comestible plan, wherein the comestible plan comprises the plurality of comestible compositions.

2. The system of claim 1, wherein the input comprises physiological data from genetic test data.

3. The system of claim 1, wherein the input comprises physiological data related to a mobility assessment.

4. The system of claim 1, wherein generating the comestible plan further comprises:
 generating the plurality of comestible compositions as a function of the positive result; and
 ordering the plurality of comestible compositions as a function of a change in the biological determinant concentration to a suitable range, wherein the plurality of comestible compositions with a highest change to the suitable range receives a highest order.

5. The system of claim 4, wherein the comestible plan includes the plurality of comestible compositions with the highest order.

6. The system of claim 1, wherein the computing device is further configured to:
 generate a musculoskeletal system disorder classifier, wherein generating the musculoskeletal system disorder classifier comprises:
  receiving musculoskeletal system disorder training data correlating a musculoskeletal system disorder and biological determinant concentration to musculoskeletal system disorder labels; and
  training the musculoskeletal system disorder classifier using the musculoskeletal system disorder training data; and
 classify, using the musculoskeletal system disorder classifier, the at least one biological determinant and the biological determinant concentration to the positive result for a musculoskeletal system disorder.

7. The system of claim 1, wherein generating the comestible plan further comprises outputting a message independent of a presence of the plurality of comestibles compositions.

8. The system of claim 1, wherein the computing device is further configured to:
 receive physical activity data; and
 update the comestible plan as a function of the physical activity data.

9. The system of claim 1, wherein the computing device is further configured to:
 receive a second input;
 redetermine the biological determinant concentration for each biological determinant; and
 update the comestible plan as a function of the second input.

10. A method for generating comestibles plan to manage a musculoskeletal system disorder, the method comprising:
 receiving, by a computing device, an input comprising physiological data;
 generating, by the computing device, a physiological data classifier, where generating the physiological data classifier comprises:
  receiving physiological data training data correlating physiological data to classes physiological data that relate to musculoskeletal disorders; and
  training the physiological data classifier using the physiological data training data;
 classifying, by the computing device and using the physiological data classifier, the physiological data to a class of physiological data relating to musculoskeletal disorders;
 extracting, by the computing device, a plurality of biological determinants of a disease state from the class of physiological data relating to musculoskeletal system disorders, wherein the plurality of biological determinants includes at least one biological determinant related to a disease state comprising at least one disorder located in musculoskeletal system;
 determining, by the computing device, a biological determinant concentration for each biological determinant of the plurality of biological determinants;
 identifying, by the computing device, a positive result for a musculoskeletal system disorder as a function of the at least one biological determinant and the biological determinant concentration; and generating by the computing device, a comestible plan as a function of the positive result, wherein generating the comestible plan comprises:
  receiving comestible plan training data;
  training a machine-learning model using the comestible plan training data, wherein the
  comestible plan training data correlates comestible compositions to effects on musculoskeletal system disorders;
  outputting a plurality of comestible compositions as a function of the machine-learning model and the positive result; and
  generating the comestible plan, wherein the comestible plan comprises the plurality of comestible compositions.

11. The method of claim 10, wherein the input comprises physiological data from genetics test data.

12. The method of claim 10, wherein the input comprises physiological data related to a mobility assessment.

13. The method of claim 10, further comprising:
  generating the plurality of comestible compositions as a function of the positive result; and
  ordering the plurality of comestible compositions as a function of a change in the biological determinant concentration to a suitable range, wherein the plurality of comestible compositions with a highest change to the suitable range receives a highest order.

14. The method of claim 13, wherein the comestible plan includes the plurality of comestibles compositions with the highest order.

15. The method of claim 10, further comprising:
  generating a musculoskeletal system disorder classifier, wherein generating the musculoskeletal system disorder classifier comprises:
    receiving a musculoskeletal system disorder training data correlating a musculoskeletal system disorder and biological determinant concentration to musculoskeletal system disorder labels; and
    training the musculoskeletal system disorder classifier using the musculoskeletal system disorder training data; and
  classifying, using the musculoskeletal system disorder classifier, the at least one biological determinant and the biological determinant concentration to a positive result for a musculoskeletal system disorder.

16. The method of claim 10, wherein generating the comestible plan further comprises outputting a message independent of a presence of the plurality of comestible compositions.

17. The method of claim 10, further comprising:
  receiving physical activity data; and
  updating the comestible plan as a function of the physical activity data.

18. The method of claim 10, further comprising:
  receiving a second input;
  redetermine the biological determinant concentration for each biological determinant; and
  updating the comestible plan as a function of the second input.

* * * * *